(12) United States Patent
Christensen et al.

(10) Patent No.: US 10,258,299 B2
(45) Date of Patent: Apr. 16, 2019

(54) PRE-OBJECT FILTER FOR SHAPING PROFILE OF RADIATION ATTENTUATION IN FAN-ANGLE DIRECTION

(71) Applicant: ANALOGIC CORPORATION, Peabody, MA (US)

(72) Inventors: Matthew B. Christensen, Peabody, MA (US); Aleksander Roshi, Peabody, MA (US); Anton M. Deykoon, Peabody, MA (US)

(73) Assignee: Analogic Corporation, Peabody, MA (US)

( * ) Notice: Subject to any disclaimer, the term of this patent is extended or adjusted under 35 U.S.C. 154(b) by 178 days.

(21) Appl. No.: 14/439,736

(22) PCT Filed: Oct. 31, 2012

(86) PCT No.: PCT/US2012/062672
§ 371 (c)(1),
(2) Date: Apr. 30, 2015

(87) PCT Pub. No.: WO2014/070151
PCT Pub. Date: May 8, 2014

(65) Prior Publication Data
US 2015/0297155 A1 Oct. 22, 2015

(51) Int. Cl.
*A61B 6/00* (2006.01)
*A61B 6/03* (2006.01)
(Continued)

(52) U.S. Cl.
CPC ............ *A61B 6/4035* (2013.01); *A61B 6/032* (2013.01); *A61B 6/06* (2013.01); *A61B 6/4078* (2013.01); *G21K 1/10* (2013.01)

(58) Field of Classification Search
CPC combination set(s) only.
See application file for complete search history.

(56) References Cited

U.S. PATENT DOCUMENTS

2003/0198319 A1* 10/2003 Toth ............... A61B 6/032
378/159
2004/0234037 A1* 11/2004 Hoffman ........... A61B 6/032
378/156
(Continued)

OTHER PUBLICATIONS

International Search Report cited in related application No. PCT/US12/62672 dated Jan. 21, 2013, pp. 10.

*Primary Examiner* — Phillip A Johnston
*Assistant Examiner* — Hsien Tsai
(74) *Attorney, Agent, or Firm* — TraskBritt

(57) ABSTRACT

Among other things, one or more systems and/or techniques are described for shaping a profile of radiation attenuation in a fan-angle direction via a pre-object filter (e.g., a bowtie filter) based upon a profile of an object. For example, a pre-object filter may be at least partially rotated about a filter axis and/or may be translated in a direction parallel to a direction of conveyance of the object under examination to adjust a profile of radiation attenuation in the fan-angle direction. Further, in one embodiment, the profile of radiation attenuation may be reshaped during rotation of the radiation source about the object to adjust an amount of radiation attenuation in the fan-angle direction (e.g., to adjust a profile of radiation attenuation as a shape of the object changes from a perspective of a radiation source as the radiation source is rotated about the object).

20 Claims, 8 Drawing Sheets

(51) Int. Cl.
*A61B 6/06* (2006.01)
*G21K 1/10* (2006.01)

(56) References Cited

U.S. PATENT DOCUMENTS

| | | | |
|---|---|---|---|
| 2005/0089146 A1* | 4/2005 | Toth | A61B 6/032 378/158 |
| 2012/0219106 A1* | 8/2012 | Stierstorfer | A61B 6/032 378/15 |

* cited by examiner

PRE-OBJECT FILTER FOR SHAPING PROFILE OF RADIATION ATTENUATION IN FAN-ANGLE DIRECTION

CROSS-REFERENCE TO RELATED APPLICATIONS

This application is a national phase entry under 35 U.S.C. § 371 of International Patent Application PCT/US2012/062672, filed Oct. 31, 2012, designating the United States of America and published in English as International Patent Publication WO 2014/070151 A1 on May 8, 2014, the entire contents and disclosure of which is hereby incorporated herein by this reference.

BACKGROUND

The present application relates to the field of imaging, and, in particular, computed tomography (CT) imaging where volumetric data of an object under examination is generated. It finds particular utility in medical applications, where a pre-object filter may be utilized to reduce a dosage of radiation applied to a patient. However, it may also find utility in security and/or industrial applications, where radiation is utilized to examine and/or image an object.

CT imaging modalities are useful to provide information, or images, of interior aspects of an object under examination. Generally, the object is exposed to radiation photons (e.g., such as X-rays, gamma rays, etc.), and an image(s) is formed based upon the radiation absorbed and/or attenuated by the interior aspects of the object, or rather an amount of photons that is able to pass through the object. Traditionally, the image(s) that is formed from the radiation exposure is a density image or attenuation image, meaning the image is colored/shaded as a function of the respective densities of sub-objects comprised within the object under examination. For example, highly dense sub-objects absorb and/or attenuate more radiation than less dense sub-objects, and thus a sub-object having a higher density, such as a bone or metal, for example, will be shaded differently than less dense sub-objects, such as muscle or clothing. However, more recently, multi-energy imaging systems (e.g., such as dual-energy CT scanners) have been utilized to discriminate sub-objects based upon more than density. Such systems are typically configured to distinguish sub-objects based upon density and other physical characteristics, such as atomic number, for example.

In some applications, such as medical imaging, it may be desirable to reduce (e.g., to a minimum) the dosage of radiation applied to a patient while achieving a desired image quality. Numerous techniques have been developed to preserve/improve image quality while reducing dosage to a patient. For example, current modulation techniques (e.g., which modulate a current applied to a radiation source) and iterative image reconstruction techniques have provided ways to preserve/improve image quality while reducing dosage to a patient. Another technique for achieving such a result is through the use of a pre-object filter, such as a bowtie filter, for example, which is inserted into a radiation beam path to shape a profile of the radiation beam to facilitate reducing dosage to a patient. Such pre-object filters have proven effective for reducing dosage (e.g., by up to 50% or more). However, due to their high cost and complexity, such pre-object filters are typically not tailored (e.g., optimized) for respective anatomical regions and/or patient sizes. For example, conventional scanners typically have, at most, two pre-object filters. A first pre-object filter corresponds to an average head size of a human patient and a second pre-object filter corresponds to an average body size of a human patient. As such, the pre-object filters may not be well suited for patients not conforming to average sizes (e.g., such as larger/smaller adults, children, etc.), causing radiation flux to less precisely match some patients relative to others.

BRIEF SUMMARY

Aspects of the present application address the above matters, and others. According to one aspect, an apparatus for a computed tomography (CT) system is provided. The apparatus comprises a pre-object filter configured to shape a profile of radiation attenuation in a fan-angle direction as a function of a profile of an object being examined. The pre-object filter is configured for at least one of translations in a direction substantially parallel to an axis of rotation for a rotating gantry of the CT system or at least partial rotation about a filter axis substantially parallel to the fan-angle direction.

According to another aspect, a method for imaging a patient is provided. The method comprises acquiring a profile of the patient, the profile describing one or more features of the patient. The method also comprises performing an imaging scan on the patient and shaping, as a function of the profile of the patient, a profile of radiation attenuation in a fan-angle direction to affect an amount of radiation attenuated in the fan-angle direction. The shaping occurs at least one of prior to performing the imaging scan or during the imaging scan.

According to yet another aspect, a computed tomography (CT) system is provided. The system comprises a radiation source, a detector array, and a rotating gantry configured to rotate the radiation source and the detector array about an object under examination. The system also comprises a pre-object filter positioned between the radiation source and the object and configured to shape a profile of radiation attenuation as a function of a profile of the object. Shaping the profile of the radiation attenuation comprises at least one of translating the pre-object filter in a direction substantially parallel to an axis of rotation for the rotating gantry, rotating the pre-object filter about a filter axis substantially parallel to a fan-angle direction, or oscillating the pre-object filter about the filter axis.

BRIEF DESCRIPTION OF THE DRAWINGS

The application is illustrated by way of example and not limitation in the figures of the accompanying drawings, in which like references indicate similar elements and in which.

DESCRIPTION

Figure 1:
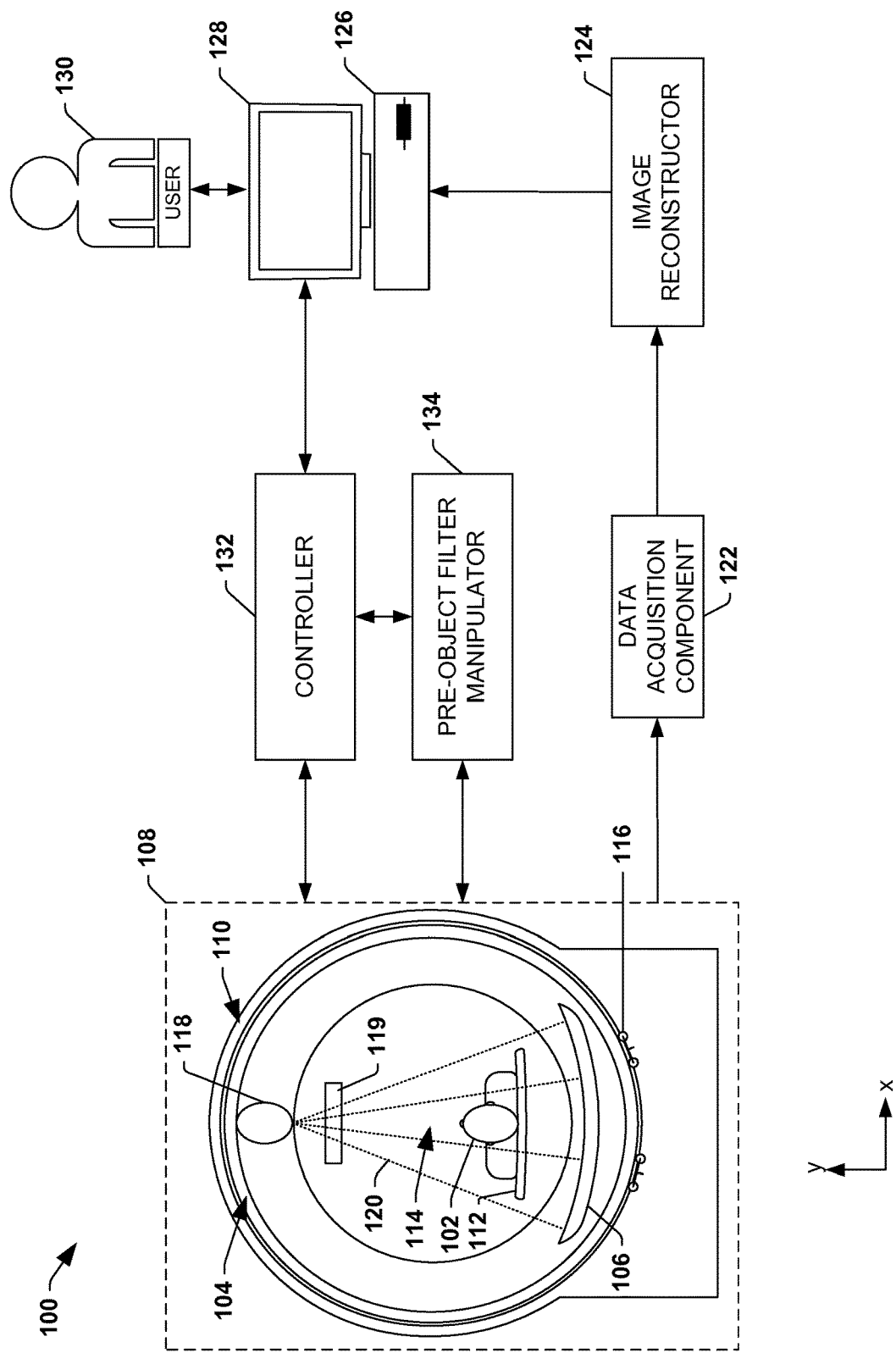
FIG. 1 is a schematic block diagram illustrating an example examination environment for examining an object.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

Among other things, one or more systems and/or techniques are described for shaping a profile of radiation attenuation in a fan-angle direction based upon a profile of an object undergoing an examination. For example, a pre-object (e.g., pre-patient) filter may be configured to adjust an amount of radiation attenuated in the fan-angle direction between examinations (e.g., of different patients and/or of different anatomical regions) and/or during an examination of a patient. Various designs of pre-object filters are described herein for shaping radiation attenuation as a function of a profile of an object to be examined and/or presently under examination. Such a profile may describe, among other things, a size of the object, a shape of the object, and/or a position of the object relative to a support article configured to support the object (e.g., a degree of off-set relative to a center line of the support article), for example. In this way, a pre-object filter configured for adjustment based upon a size, shape, and/or location of an object, for example, may (e.g., dynamically) adjust an amount of radiation attenuated in the fan-angle direction in a desired manner, for example.

Shaping a profile of radiation attenuation via the pre-object filter based upon the profile of the object may, for example, reduce the dosage of radiation to the object while providing desired imaging specification (e.g., a specified imaging quality). Moreover, in one embodiment, by shaping a profile of radiation attenuation based upon the profile of the object, radiation flux impinging a detector array may be substantially equalized, which may be particularly useful with respect to photon counting and/or energy discriminating detector arrays (e.g., which may have a limited dynamic range relative to charge integrating detector arrays). That is, by substantially equalizing flux via the pre-object filter, pulse pile-up (e.g., caused by high flux rates) may be mitigated. Moreover, even with respect to charge integrating detector arrays, equalizing flux may be beneficial to facilitate the use of higher gains (e.g., which may improve noise performance (e.g., signal-to-noise ratio) and therefore result in better image quality and/or better low contrast detectability), for example.

FIG. 1 illustrates an example environment 100 wherein one or more of the techniques and/or systems described herein may find applicability. More particularly, FIG. 1 illustrates an example computed tomography (CT) system configured to examine an object(s) 102 (e.g., a patient, suitcase, etc.) and generate one or more images therefrom. It may be appreciated that while specific reference is made herein to CT systems, the instant application may find applicability to other radiation imaging systems (e.g., such as digital/projection radiology, mammography, etc.) where varying an amount of radiation attenuation in a fan-angle direction may be useful, and thus is not limited to CT.

In the example environment 100, an examination unit 108 of the imaging modality is configured to examine one or more objects 102 (e.g., human patients, animal patients, bags, etc.). The examination unit 108 can comprise a rotating gantry 104 and a (stationary) support structure 110 (e.g., which may encase and/or surround as least a portion of the rotating gantry 104 (e.g., as illustrated with an outer, stationary ring, surrounding an outside edge of an inner, rotating ring)). During an examination of the object(s) 102, the object(s) 102 can be placed on a support article 112, such as a bed or conveyor belt, for example, that is selectively positioned in an examination region 114 (e.g., a hollow bore in the rotating gantry 104), and the rotating gantry 104 can be rotated and/or supported about the object(s) 102 by a rotator 116, such as a motor, drive shaft, chain, roller truck, etc.

The rotating gantry 104 may surround a portion of the examination region 114 and may comprise a radiation source 118 (e.g., an ionizing x-ray source, gamma radiation source, etc.) and a detector array 106 that is mounted on a substantially diametrically opposite side of the rotating gantry 104 relative to the radiation source(s) 118. During an examination of the object(s) 102, the radiation source(s) 118 emits fan, cone, wedge, and/or other shaped radiation 120 configurations from a focal spot(s) of the radiation source 118 (e.g., a region within the radiation source 118 from which radiation 120 emanates).

The example environment 100 further comprises a pre-object filter 119. The pre-object filter, which may be positioned between the radiation source 118 and the examination region 114 (and more particularly, the object 102), is configured to attenuate, in a fan-angle direction, at least a portion of the emitted radiation 120 to shape the emitted radiation 120. Such shaping may occur during an examination of the object 102 and/or between examinations of different objects. By way of example, prior to an imaging scan (e.g., from which diagnostic images are generated), a profile of the object 102 may be developed (e.g., using a pre-scan technique and/or by entering measurements of the object 102 into the CT system). Using this profile, a pre-object filter manipulator 134 may be configured to generate instructions for adjusting the pre-object filter (e.g., to shape a profile of radiation attenuation in the fan-angle direction as a function of the object being scanned). Further, in another embodiment, the pre-object filter manipulator may receive information pertaining to a present gantry rotation angle and/or a rotation speed for the rotating gantry 104, and the pre-object filter manipulator 134 may adjust the pre-object filter based upon the gantry rotation angle and/or a speed of rotation, for example.

The pre-object filter manipulator (e.g., which may be located on the stationary side of the imaging modality and/or on the rotating gantry 104), may be configured to provide information to the pre-object filter 119 regarding adjustment information, such as how the pre-object filter 119 is to be translated, rotated, and/or oscillated, for example. In one embodiment, such adjustment information may be provided based upon the profile of the object 102. In another embodiment, the pre-object filter manipulator 134 may be configured to receive information relating to the rotating gantry 104 from a controller 132, such as information corresponding to a speed of rotation, and the object filter manipulator may be configured to specify how the pre-object filter is to be adjusted based upon the information relating to the rotating gantry 104, for example.

Emitted radiation 120 that traverses the object(s) 102 may be attenuated differently by different aspects of the object(s) 102. Because different aspects attenuate different amounts of the radiation 120, an image(s) may be generated based upon the attenuation, or variations in the number of photons that are detected by cells of the detector array 106. For example, more dense aspects of the object(s) 102, such as a bone or metal plate, may attenuate more of the radiation 120 (e.g., causing fewer photons to strike the detector array 106) than less dense aspects, such as skin or clothing.

The detector array 106 is configured to directly convert and/or indirectly convert detected radiation into signals that can be transmitted from the detector array 106 to a data acquisition component 122 configured to compile signals that were transmitted within a predetermined time interval, or measurement interval, using various techniques (e.g., integration, photon counting, etc.). It may be appreciated that such a measurement interval may be referred to as a "view" and generally reflects signals generated from radiation 120 that was emitted while the radiation source 118 was at a particular angular range relative to the object(s) 102. Based upon the compiled signals, the data acquisition component 122 can generate projection data indicative of the compiled signals, for example.

The example environment 100 also illustrates an image reconstructor 124 that is operably coupled to the data acquisition component 122 and is configured to generate one or more images representative of the object(s) 102 under examination based at least in part upon signals output from the data acquisition component 122 using suitable analytical, iterative, and/or other reconstruction technique (e.g., tomosynthesis reconstruction, filtered back-projection, iterative reconstruction, etc.). For example, in a CT imaging application, the image reconstructor 124 may be configured to generate one or more image slices of the object(s) 102, respectively representative of a portion, or slice, of the object(s) 102. Such image slices may be combined, for example, to generate one or more images for presentation to a user 130, for example.

The example environment 100 also includes a terminal 126, or workstation (e.g., a computer), configured to receive image(s) from the image reconstructor 124, which can be displayed on a monitor 128 to a user 130 (e.g., security personnel, medical personnel, etc.). In this way, the user 130 can inspect the image(s) to identify areas of interest within the object(s) 102. The terminal 126 can also be configured to receive user input which can direct operations of the object examination apparatus 108 (e.g., a speed of gantry rotation, an energy level of the radiation, etc.).

In the example environment 100, a controller 132 is operably coupled to the terminal 126. In one example, the controller 132 is configured to receive user input from the terminal 126 and generate instructions for the examination unit 108 indicative of operations to be performed (e.g., such as a rotation speed of the rotating gantry 104). The controller 132 may also be configured to receive information from the examination unit 108, such as, for example, information related to a gantry rotation angle.

It may be appreciated that the components of the illustrated CT imaging modality and/or the features described with respect to respective components are intended to provide an example configuration and are not intended to be construed as limiting the scope of the instant application, including the claims. That is, an imaging modality may comprise additional components and/or different components than those described above and/or one or more of the described components may be configured to perform additional and/or different actions. Moreover, the arrangement of components may be different than the illustrated arrangement. For example, in one embodiment, the data acquisition component 122 may be coupled to the detector array 106 and mounted to the rotating gantry 104.

Figure 2:
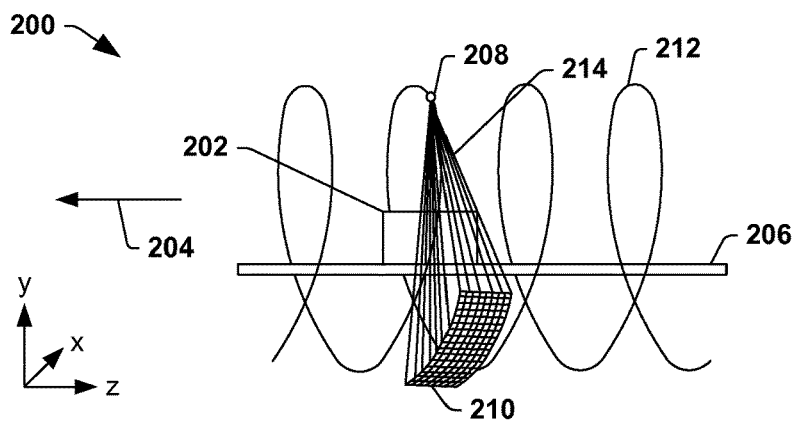
FIG. 2 illustrates a functional diagram of a helical CT imaging modality.

FIG. 2 is a functional diagram 200 of a helical scan performed via a CT imaging modality, such as in medical and/or security applications. In such an imaging modality, an object 202 (e.g., 102 in FIG. 1) under examination is translated 204 (e.g., at either constant speed or in a step-and-shoot manner) in a direction parallel to an axis of rotation (e.g., the object is translated along a z-axis), via an object support 206 (e.g., 112 in FIG. 1). During the translations and/or between translations, one or more radiation sources 208 (e.g., 118 in FIG. 1) and a detector array 210 (e.g., 106 in FIG. 1) are rotated about the object. In this way, a helical scan of the object is performed (e.g., where the radiation source(s) 208 and detector array 210 do not move in the z-direction, and thus the helical trajectory 212 is established by the combination of the x/y rotation of the source 208 and detector array 210 and the z-direction translation 204 of the object 202). It may be appreciated that as used herein, helical scan, helical scanning, and/or the like is intended to describe both translation of the object at a constant speed and periodic translation (e.g., such as performed with respect to step-and-shoot).

It may be appreciated that for purposes of the instant application, the z-direction (e.g., at times also referred to as axial direction) may be defined as a direction parallel to the axis of rotation. Typically, the object 202 is translated in the z-direction. The detector array 210 may be said to have a z-direction and an x-direction (e.g., although it may have some y-component due to an arcuate shape of the detector array 210). Thus, the x-direction may be a direction of the detector array 210 that is perpendicular to the z-direction. The y-direction may be defined as the dimension extending between the radiation source 208 and the detector array 210. Typically, the trajectory of radiation is predominately in the y-direction, although the trajectory may have an x-component or a z-component. It may be appreciated that relative orientations may change as elements rotate and/or move (e.g., because the dimensions, as defined, track the radiation source 208 and detector array 210).

Radiation 214 may be emitted from the radiation source 208 in a multitude of directions. In one example, emitted radiation 214 may form a cone shape (e.g., in x, y and z directions) as it emanates from the radiation source 208 to the detector array 210, which may at times be referred to as a cone beam. In another example, emitted radiation 214 may form a fan shape (e.g., in x, y directions) as it emanates from the radiation source 208 to the detector array 210, which may at times be referred to as a fan beam. It may be appreciated that a cone beam may be said to comprise one or more fan beams. For example, where a fan beam is comprised within an x, y plane, a cone beam may comprise multiple fan beams that are 'stacked' on top of one another or adjacent to one another in the z direction. Adjacent fan beams (that represent slices through the conical shaped cone beam) may vary in width, where a centermost fan beam (slicing through the greatest diameter of the cone beam) may have a greatest width and outmost fan beams may have a smallest width.

For purposes of the instant application, the trajectory of emitted radiation may be described in terms of at least two directional components: a cone-angle direction and a fan-angle direction. The cone-angle direction typically refers to a direction substantially parallel to the axis of rotation for the rotating gantry. The fan-angle direction typically refers to a direction substantially perpendicular to the axis of rotation for the rotating gantry and describes a direction in which the fan spreads out (e.g., a direction along which the fan elongates or becomes wider as radiation moves from the source 208 to the detector array 210). Thus, based upon the foregoing definitions of the x, y, and z, directions, the cone-angle direction may be described as the z-direction and the fan-angle direction may be described as the x-direction.

Also for purposes of the instant application, a gantry rotation angle is generally defined as a number of degrees that the rotating gantry has rotated away from a predefined zero-degree reference. For example, 0 degrees may be defined as a position of the rotating gantry that causes the radiation source 208 to be positioned directly above the object 202. Thus, when the rotating gantry rotates (e.g., within the x, y plane) such that the radiation source 208 becomes positioned directly below the object 202 (and the detector array 210 is directly above or over the object 202), the gantry rotation angle may be approximately 180 degrees.

A pre-object filter (e.g., such as a bow-tie filter) is configured to shape a profile of radiation attenuation in the fan-angle direction (e.g., x-direction) by attenuating at least some radiation emitted in the fan-angle direction more than other radiation emitted in the fan-angle direction. Typically, the portion of the radiation that is attenuated to a greater degree by the pre-object filter is a portion of the radiation that may not be attenuated by the object (e.g., because the trajectory of the radiation does not intersect the object). In this way, the pre-object filter facilitates reducing significant differences in radiation flux received at different portions of the detector array.

Figure 3:
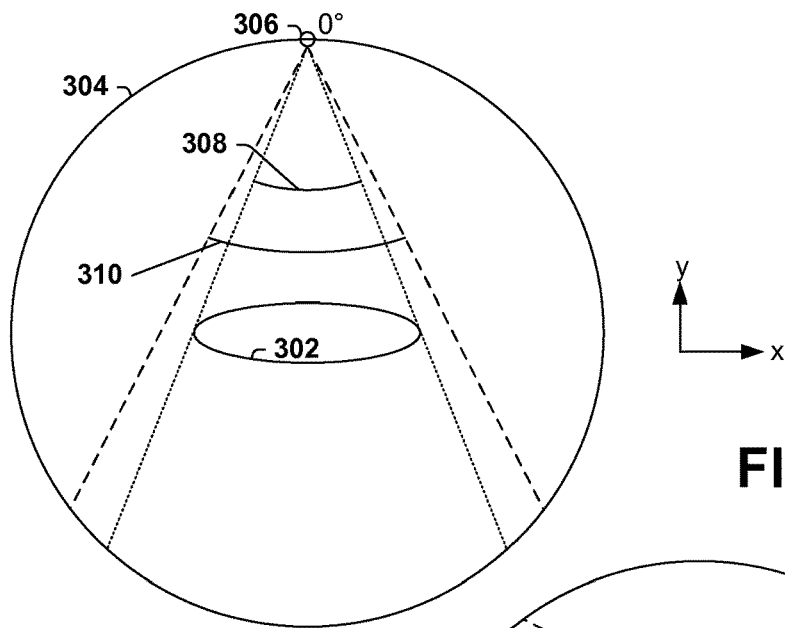
FIG. 3 illustrates how a pre-object filter may shape a profile of radiation attenuation in a fan-angle direction based upon a profile of an object.
Figure 4:
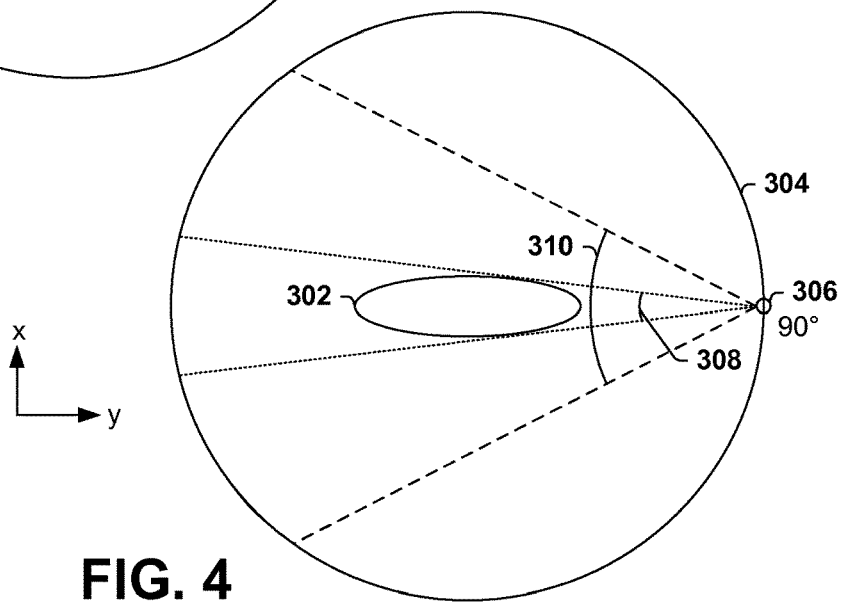
FIG. 4 illustrates how a pre-object filter may shape a profile of radiation attenuation in a fan-angle direction based upon a profile of an object.

As used herein, fan-angle 310 and/or the like is intended to describe an overall angle at which radiation fans out (e.g., in the x-direction), and unattenuated fan-angle 308 and/or the like is intended to describe a portion of the fan-angle corresponding to radiation intended to intersect the object and thus is attenuated to a lesser degree by the pre-object filter (e.g., relative to the remainder of the fan-angle corresponding to radiation that is attenuated by the pre-object filter). It may thus be appreciated that 'unattenuated' fan-angle does not necessarily mean zero percent attenuation, but rather some reduction in attenuation as compared to attenuation of radiation in other parts of the fan angle. As an example, FIGS. 3-4 illustrate how a pre-object filter may shape a profile of radiation attenuation in the fan-angle direction based upon a profile (e.g., a size and/or shape) of an object. More particularly, FIGS. 3-4 illustrate an elliptically shaped object 302 (e.g., which may approximate a cross-section through a torso of a human patient) undergoing an examination/scan. The outer circle 304 represents a trajectory of a rotating gantry supporting a radiation source 306 (e.g., 208 in FIG. 2) and a detector array (not shown).

In the example embodiment, the object 302 is wider when viewed from the top or bottom of the page (e.g., 0 degrees or 180 degrees) than when viewed from the side (e.g., 90 degrees or 270 degrees). Thus, it may be desirable to adjust the unattenuated fan-angle 308 during an examination according to the orientation of the radiation source 306 (e.g., or a gantry rotation angle of the rotating gantry) relative to the object 302. For example, when the radiation source 306 is at 0 degrees as illustrated in FIG. 3, a larger portion of radiation emitted in the fan-angle direction has a trajectory that intersects the object 302 than when the radiation source is at 90 degrees as illustrated in FIG. 4. As such, the pre-object filter may be configured to attenuate a greater portion of the radiation in the fan-angle direction at 90 degrees than at 0 degrees, causing the unattenuated fan-angle 308 to be smaller at 90 degrees (FIG. 4) than at 0 degrees (FIG. 3). It will thus be appreciated that the pre-object filter may (e.g., dynamically) shape a profile of radiation attenuation in the fan-angle direction (e.g., and vary an amount of radiation attenuated) as the rotating gantry rotates (e.g., through different gantry rotation angles) and views the object from different perspectives. In this manner, the unattenuated fan-angle 308 is adjusted as the rotating gantry rotates during a scan of the object.

Figure 5:
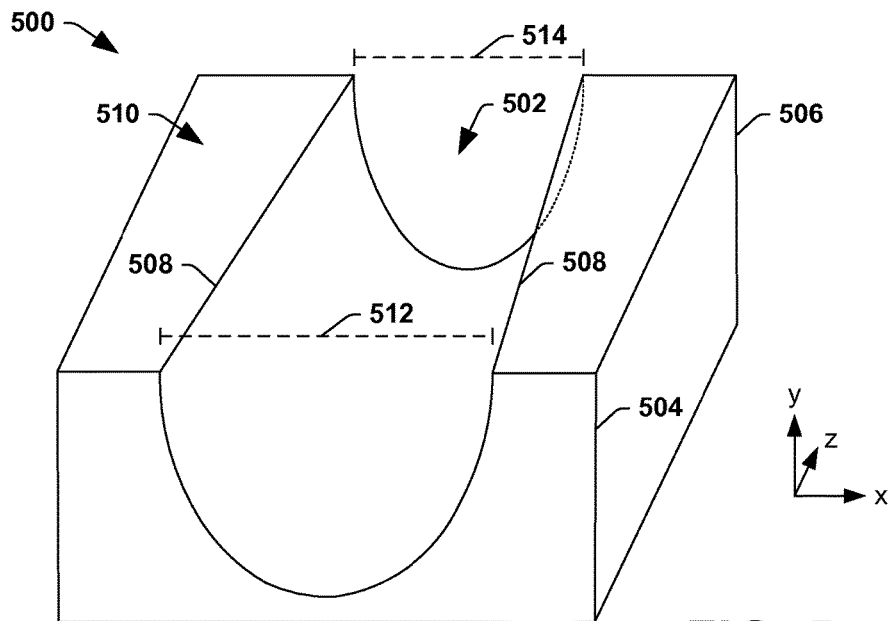
FIG. 5 illustrates an example pre-object filter.

FIG. 5 illustrates an example pre-object filter 500 configured to shape a profile of radiation attenuation in a fan-angle direction as a function of a profile of an object being examined. Such a pre-object filter 500 may be comprised of aluminum, copper, Teflon, and/or other materials that are at least partially opaque to radiation (e.g., and can thus attenuate a portion of the radiation impinging the pre-object filter 500). In another embodiment, at least some of the pre-object filter 500 may be comprised of a less radiation opaque material(s) than the foregoing described materials.

The example pre-object filter 500 defines a channel 502 extending in a direction substantially parallel to the axis of rotation for a rotating gantry (e.g., extending in the z-direction) from a first end 504 of the pre-object filter 500 to a second end 506 of the pre-object filter 500. In the illustrated embodiment, a sidewall 508 of the pre-object filter 500 that defines the channel 502 is curved such that a cross-section of the channel 502 (e.g., illustrating an x-y plane) may have the shape of a parabola. In other embodiments, the sidewall 508 may be shaped differently, causing the shape of the channel 502 to be different. For example, in another embodiment, sections of the sidewall 508 may meet at 90-degree angles, causing a cross-section of the channel 502 to appear more rectangular or square. Further, while the illustrated embodiment provides for the channel 502 extending from the first end 504 to the second end 506 of the pre-object filter 500, in another embodiment, the channel 502 may not extend the entire length of the pre-object filter 500. As such, at least one of the first end 504 and/or the second end 506 may not be shaped to facilitate the channel 502 (e.g., to provide an entry-way into the channel 502).

As illustrated, the channel 502 is formed through on a top surface 510 of the pre-object filter 500 (e.g., such that the channel 502 is accessible through the top surface 510). In another embodiment, the channel 502 may be a hollow bore in the pre-object filter 500, which is enclosed by the sidewall 508 and the top surface 510 (e.g., such that the channel 502 takes that shape of a tunnel carved into and/or through the pre-object filter 500).

The pre-object filter 500 may be shaped such that the width (e.g., measured in the x-direction) of the channel 502 decreases from the first end 504 to the second end 506. For example, a width 512 of the channel 502 at or near the first end 504 (e.g., at a first cross-sectional slice through the channel 502) may be greater than a width 514 of the channel 502 at or near the second end 506 (e.g., at a second cross-sectional slice). As such, a volume of a cross-sectional slice associated with (e.g., proximate) the first end 504 may be less than a volume of a (e.g., same number of) cross-section slice associated with (e.g., proximate) the second end 506 because the channel 502 occupies a larger amount of space proximate the first end 504 than proximate the second end 506, for example.

In the illustrated embodiment, the width of the channel 502 decreases smoothly from the first end 504 to the second end 506 (e.g., such that the sidewall 508 is smooth from the first end 504 to the second end 506). In another embodiment, the width of the channel 502 may decrease in a non-uniform manner, such as, for example, incrementally in a stair-step manner between the first end 504 and the second end 506 (e.g., causing the sidewall 508 to appear jagged).

Typically, at any given time, radiation passes through merely a relatively small cross-sectional slice of the pre-object filter 500 (e.g., where the thickness of the slice is defined by the z-dimension of the slice). The thicker the pre-object filter 500 (in the y-dimension), the greater the amount of radiation that is attenuated. Thus, radiation having a trajectory through the channel 502 may experience less attenuation than radiation having a trajectory through portions of the pre-object filter 500 that do not comprise the channel 502 (e.g., and are thus thicker in the y-dimension). To alter which portion (or cross-sectional slice) of the pre-object filter 500 is exposed to radiation, the pre-object filter 500 may be configured for translation in a direction parallel to the axis of rotation and/or parallel to the channel 502 (e.g., in the z-direction). By moving (e.g., translating in the z-direction) the pre-object filter 500 from a first position to a second position, the unattenuated fan-angle (e.g., corresponding to radiation traversing the channel 502 and thus being attenuated to a lesser degree) is increased/decreased to decrease/increase the amount of radiation that is attenuated by the pre-object filter 500. For example, if the pre-object filter 500 was translated to cause the second end 506 to be exposed to radiation as opposed to the first end 504, a greater amount of radiation may be attenuated (e.g., because the first end 504 is configured to attenuate a lesser amount of radiation due to the channel 502 being wider at the first end 504 than at the second end 506). In this way, the pre-object filter 500 can periodically (re)shape a profile of radiation attenuation (e.g., and alter an amount of radiation attenuated by the pre-object filter 500 (e.g., causing the unattenuated fan-angle to change as a function of which portion of the pre-object filter 500 is exposed to radiation)).

Further, in one embodiment, the pre-object filter may be configured for translation in a direction substantially parallel to the fan-angle direction. By way of example, in some embodiments an object undergoing examination may be off-set relative to a center line of the support article, where the center line extends parallel to the axis of rotation. Accordingly, the pre-object filter may be translated in the fan-angle direction (e.g., moved left or right when looking into gantry bore) to correspond to the off-set such that a center line of the channel (e.g., extending parallel to the axis of rotation) is substantially matched to the off-set of the object (e.g., so that a center line of the patient aligns with a center line of the channel). Further, where a region-of-interest that is not positioned at an isocenter of the detector array, the pre-object filter 500 may be configured for motion in the fan-angle direction to follow the region-of-interest, for example.

Movement or translations of the pre-object filter 500 may be controlled, for example, by a stepper motor or other motor, which may be controlled by a pre-object filter manipulator (e.g., 134 in FIG. 1), for example. In one embodiment, such a pre-object filter manipulator may be configured to receive information related to a rotating gantry (e.g., 104 in FIG. 1) and/or a support article (e.g., 112 in FIG. 1) from a controller (e.g., 132 in FIG. 1) to substantially synchronize translation of the pre-object filter 500 with the rotating gantry and/or support article, for example.

Numerous modes for moving and/or translating the pre-object filter 500 are contemplated and a desired mode may be a function of, among other things, the intended application and/or desired functionality of the pre-object filter 500. For example, in a first mode, the pre-object filter 500 may be translated prior to and/or at a beginning of an imaging scan of an object such that a portion of the pre-object filter 500 that corresponds to a (e.g., cross-sectional) shape of the object is exposed to radiation (e.g., such that the unattenuated fan-angle more closely approximates a width of the object upon which radiation impinges). During the imaging scan, or the remaining portion of the imaging scan, the position of the pre-object filter 500 may or may not change as a function of the rotating gantry angle and/or the position/movement of the support article, for example.

In a second mode, the pre-object filter 500 may be translated during the imaging scan based upon movement of the support article and/or rotation of the rotating gantry. In this way, the profile of the radiation attenuation is (e.g., periodically) re-shaped during the imaging scan and/or an amount of radiation attenuated in a fan-angle direction is adjusted during the imaging scan (e.g., the unattenuated fan-angle 308 is varied during the imaging scan). By way of example, an object (e.g., such as a human patient) may not be uniformly shaped. For example, a width of a patient's head is typically less than a width of the patient's shoulders. When an imaging scan involves imaging the patient's head and the patient's shoulders, it may be desirable to translate the pre-object filter 500 to cause a narrower portion of the channel 502 (e.g., proximate the second end 506) to be exposed to radiation when scanning the patient's head (e.g., to attenuate a greater amount of radiation in the fan-angle direction and to reduce an unattenuated fan-angle) and to cause a wider portion of the channel 502 (e.g., proximate the first end 504) to be exposed to radiation when scanning the patient's shoulders (e.g., to attenuate a smaller amount of radiation in the fan-angle direction and to increase an unattenuated fan-angle). Thus, the pre-object filter 500 may be translated so as to track a patient's size during the imaging scan.

In a third mode, the pre-object filter 500 may be translated in a direction parallel to the axis of rotation (e.g., in the z-direction) during the imaging scan based upon a gantry angle of the rotating gantry to track, for example, changes in a size of an object from a front face, to a side face, to a rear face, and back to a side face. For example, typically, a human patient is wider when viewed from the front and back than when viewed from a side. As such, the pre-object filter 500 may translate during the rotation to cause less radiation to be attenuated when the radiation source is facing a front (e.g., at 0 degrees) or a back (e.g., at 180 degrees) of the patient than when facing a side (e.g., 90 or 270 degrees) of the patient. By way of example, a portion of the channel 502 having a larger width (e.g., proximate the first end 504) may be exposed to radiation or intervene between the patient and the radiation source when the gantry angle indicates that the radiation source is facing a front or back of a patient, and a portion of the channel 502 having a smaller width (e.g., proximate the second end 506) may be exposed to or intervene between the patient and the radiation source when the gantry angle indicates that the radiation source is facing a side of a patient. In this way, the profile of the radiation attenuation and unattenuated fan-angle may be (e.g., dynamically) altered during the rotation (e.g., as shown in FIG. 3) based upon the gantry angle, for example.

Other modes for translating the pre-object filter 500 may include a combination of the modes described above, such as a combination of the second mode and the third mode.

Figure 6:
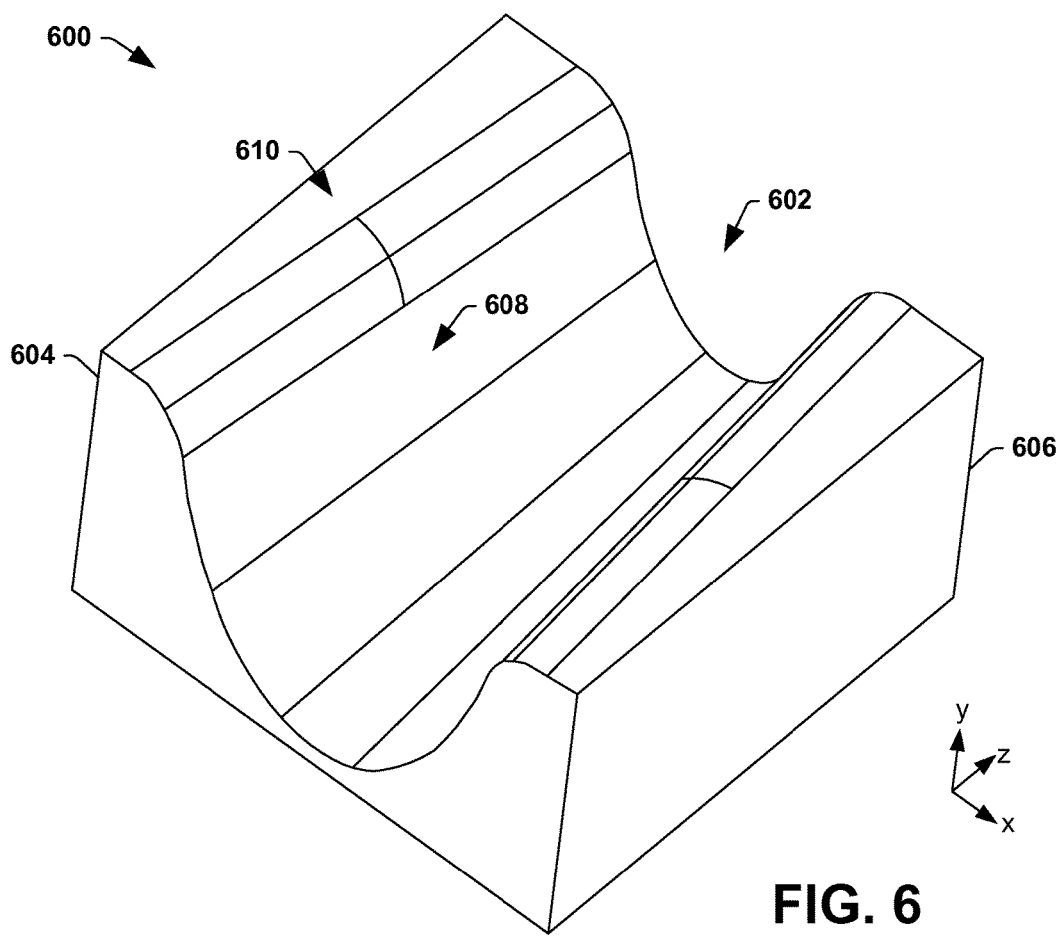
FIG. 6 illustrates an example pre-object filter.

FIG. 6 illustrates another example pre-object filter 600 configured similarly to the pre-object filter 500 in FIG. 5, where a channel 602 extends in a direction parallel to the axis of rotation of a rotating gantry from a first end 604 to a second end 606 and is defined by a side-wall 608 of the pre-object filter 600. Whereas the sidewall 508 of the pre-object filter 500 is illustrated as meeting the top surface 510 abruptly at a substantially 90-degree angle, the sidewall 608 of pre-object filter 600 transitions more gradually or fluidly into the top surface 610 (e.g., as made visible by the lines drawn on the surface of the channel). It may be appreciated that such a difference may be a design preference and/or may be intended to soften a transition between heavily attenuated radiation traversing thick portions of the sidewall 608 and less attenuated radiation traversing the channel 602 and/or thinner portions of the sidewall 608. As illustrated in FIG. 5, a width of the channel 602 changes between the first end 604 and the second end 606 (e.g., such that the channel 602 narrows from the first end 604 to the second end 606). In this way, an amount of radiation attenuation in the fan-angle direction may be altered and/or a profile of radiation attenuation may be reshaped by translating the pre-object filter 600 in a direction substantially parallel to the channel 602, for example.

Figure 7:
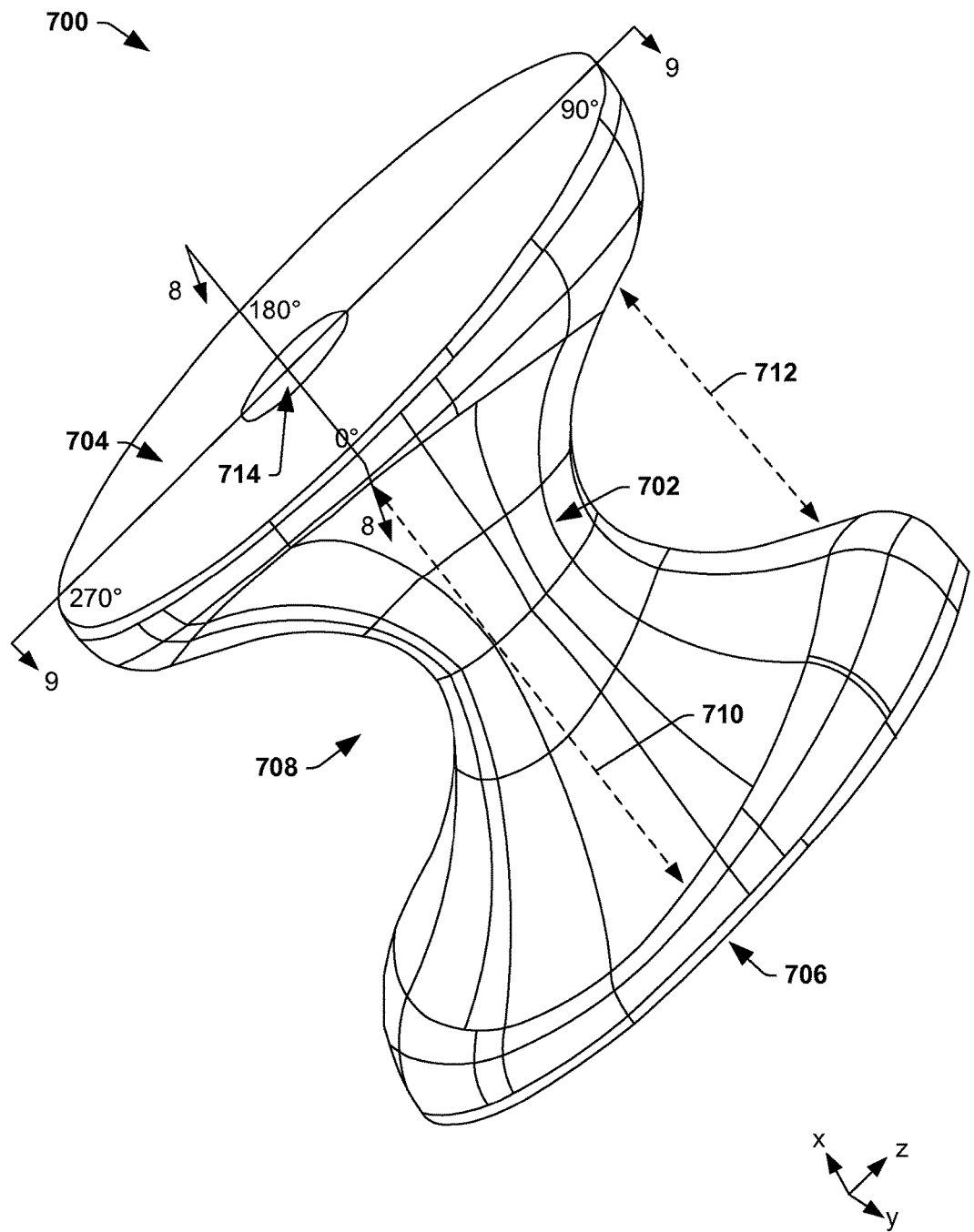
FIG. 7 illustrates an example pre-object filter.

FIG. 7 illustrates yet another example of a pre-object filter 700 configured to shape a profile of radiation attenuation in a fan-angle direction as a function of a profile of an object being examined. In this way, an amount of radiation attenuated in the fan-angle direction (e.g., x-direction) may be adjusted (e.g., altering an unattenuated fan-angle) based upon a shape of the object, before an imaging scan of an object is performed and/or during the imaging scan. Such a pre-object filter 700 may be comprised of aluminum, cooper, Teflon, and/or other materials that are at least partially opaque to radiation (e.g., and can thus attenuate a portion of the radiation directed toward the pre-object filter 500), for example.

The pre-object filter 700 is configured for rotation about a filter axis extending in the fan-angle direction (e.g., the x-direction. Further, in one embodiment, the pre-object filter 700 may be configured for translation in the fan-angle direction to track a region of interest and/or to track an object that is offset from a center line of the support article, for example.

A core 702 of the pre-object filter 700 is situated between a first end 704 and a second end 704 of the pre-object filter 700 and connects the first end 704 to the second end 706. The core 702 may comprise a parameter (e.g., circumference), measured at a mid-point between the first end 704 and the second end 706, that is smaller than a parameter (e.g., circumference) of the first end 704 and/or smaller than a parameter (e.g., circumference) of the second end 706. In this way, an aperture 708 (e.g., a valley) may be defined by the first end 704, the second end 706 and the core 702. That is, for example, an aperture 708 may formed by the smaller parameter core 702 and the larger parameter first end 704 and/or second end 706. In one embodiment, such an aperture 708 may extend substantially 360 degrees about the pre-object filter 700.

In the illustrated embodiment, a parameter (circumference) of the core 702 decreases gradually from the first end 704 and/or from the second end 706 toward a center of the core 702 (e.g., laying substantially midway between the first end 704 and the second end 706). In another embodiment, the parameter of the core 702 may decrease non-uniformly (e.g., in a stair-step fashion). As such, in another embodiment, an exposed sidewall of the core 702 may appear more jagged than the relatively smooth sidewall of the illustrated core 702.

A width of the aperture 708 may differ between a first rotational angle of the pre-object filter 700 and a second rotational angle of the pre-object filter 700. As an example, the aperture 708 may measure a first width 710 at a first rotational angle (e.g., of 0 degrees) and may measure a second width 712 at a second rotational angle (e.g., at 90 degrees). In one embodiment, the widest portion of the aperture 708 is separated from the narrowest portion of the aperture 708 by approximately 90 degrees, and the width of the aperture 708 may continuously and/or incrementally decrease between the widest portion and the narrowest portion, for example. By way of example, the aperture 708 may be widest at the first rotational angle (e.g., which measures the first width 710) and may be narrowest at the second rotational angle (e.g., which measures the second width 712). The width the aperture 708 may gradually vary between various rotational angles, for example.

Further, in one embodiment, the aperture 708 may gradually increase in width between the second rotational angle and a third rotational angle separated from the second rotational angle by 90 degrees (e.g., the third rotation angle may be at 180 degrees). At the third rotational angle, the width of the aperture 708 may be equal to the first width 710, for example. Further, between the third rotational angle and a fourth rotation angle separated from the third rotation angle by 90 degrees (e.g., the fourth rotation angle may be at 270 degrees), the aperture 708 may gradually decrease in width until, at the fourth rotation angle, the width of the aperture substantially equals the second width 712, for example. It can thus be appreciated that a first half of the pre-object filter 700 may be substantially symmetrical to a second half of the pre-object filter 700, such that the width of the aperture 708 at a given rotational angle substantially matches a width of the aperture 708 at another rotational angle 180 degrees from the given rotational angle, for example.

Figure 8:
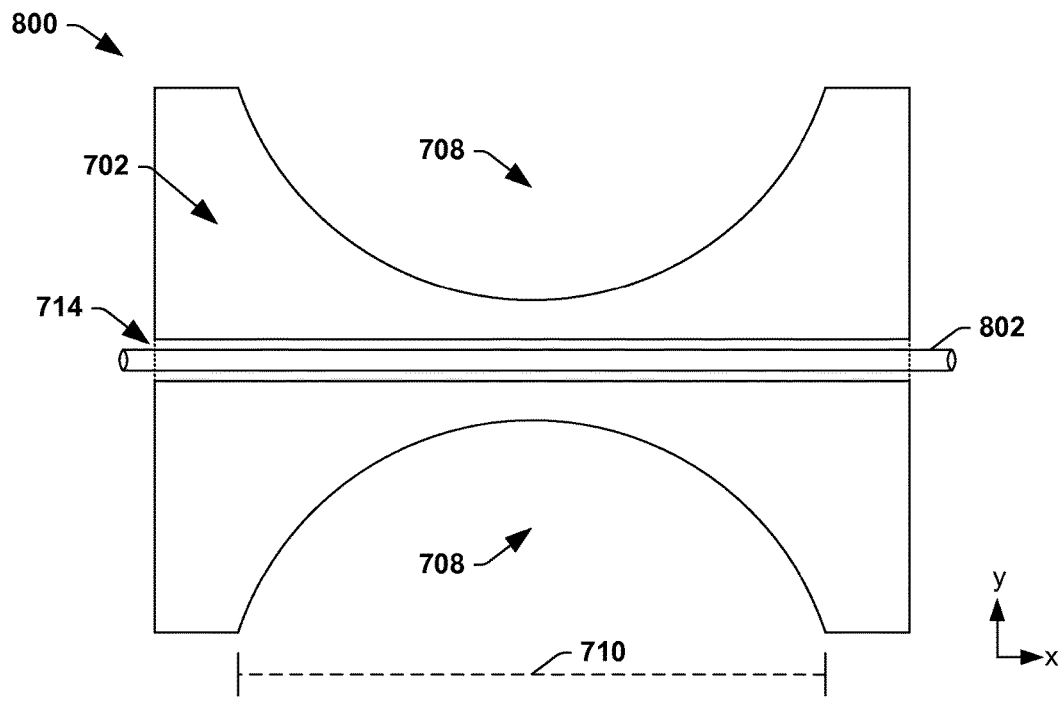
FIG. 8 illustrates a cross-section through an example pre-object filter.
Figure 9:
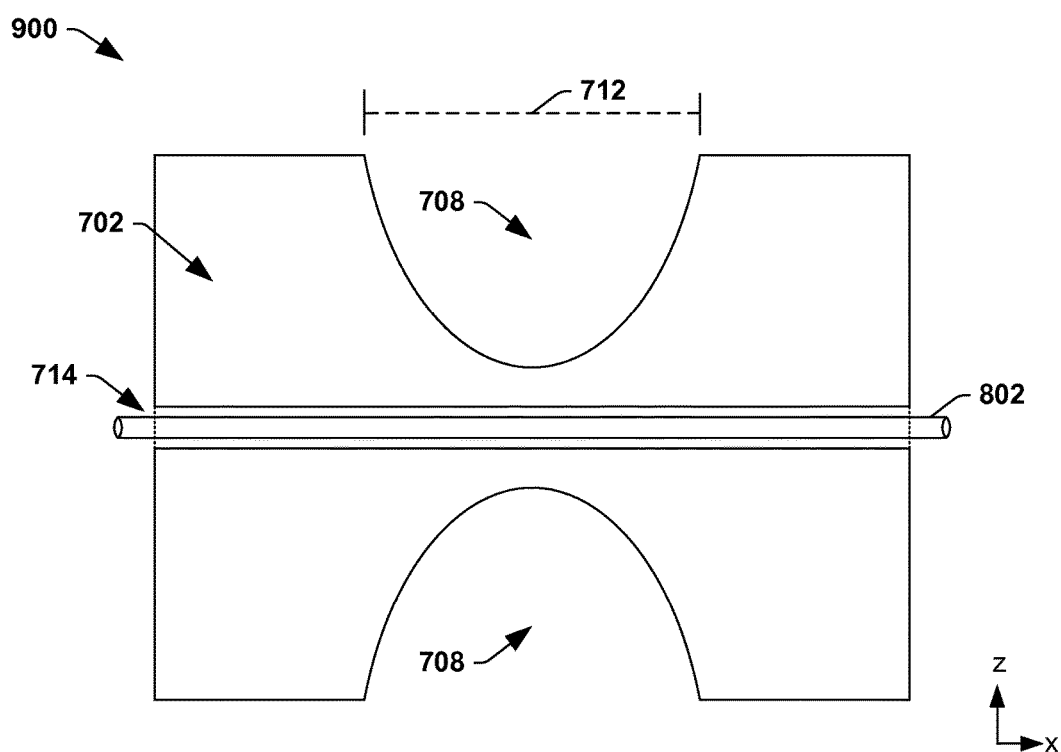
FIG. 9 illustrates a cross-section through an example pre-object filter.

FIGS. 8-9 illustrate cross-sections of the pre-object filter 700, and depict how a width of the aperture 708 changes at various rotation angles. More particularly, FIG. 8 illustrates a cross-sectional view 800 of the pre-object filter 700 taken along line 8-8 in FIG. 7, and FIG. 9 illustrates a cross-section view 900 of the pre-object filter 700 taken along line 9-9 in FIG. 7. Thus, FIG. 8 may illustrate a cross-sectional view 800 depicting a plane of the pre-object filter 700 at the first and third rotational angles (e.g., where the aperture 708 is widest), and FIG. 9 may illustrates a cross-sectional view 900 depicting a plane of the pre-object filter at the second and fourth rotational angles (e.g., where the aperture 708 is narrowest).

A tube 802 or central core about which the pre-object filter 700 is configured to rotate may extend through a center 714 of the pre-object filter 700 in a direction parallel to the filter axis and/or perpendicular to an axis of rotation for a rotating gantry of a CT system, for example (e.g., the tube 802 may extend in the x-direction). In one embodiment, such a tube 802 or central core may be hollow and/or may comprise one or more low attenuation materials having structural integrity to support the pre-object filter.

Surrounding the tube 802 may be the core 702, which may comprise radiation attenuating material(s), such as copper, aluminum, Teflon and/or other materials configured to attenuate at least a portion of the radiation contacting the pre-object filter 700. Such radiation attenuating material may be shaped to form an aperture 708 having a desired width(s). For example, as illustrated in the cross-sectional view 800 (e.g., taken along line 8-8 in FIG. 7), the aperture 708 measures a first width 710 at a first rotational angle (e.g., 0 degrees) and a third rotational angle (e.g., 180 degrees). As illustrated in the cross-sectional view 900 (e.g., taken along line 9-9 in FIG. 7), at the second rotational angle (e.g., 90 degrees) and the fourth rotational angle (e.g., 270 degrees), the aperture 708 measures a second width 712, different than the first width 710. It may be appreciated that a maximum depth of the aperture 708 (e.g., measured in the y-direction) in FIGS. 8-9 may be substantially equal at all or substantially all of the rotational angles, even though a profile of the aperture 708 changes at different rotational angles.

The pre-object filter 700 is configured for rotation by the tube 802 about the filter axis, which is substantially parallel to the fan-angle direction. For example, in the illustrated embodiment, the filter axis may extend in the x-direction. In one embodiment, the pre-object filter 700 may also be configured for movement in the fan-angle direction. Movement of the pre-object filter 700 may be controlled by a stepper motor or other motor, which may be controlled by a pre-object filter manipulator (e.g., 134 in FIG. 1), for example.

Numerous modes for at least partially rotating the pre-object filter 700 about the filter axis are contemplated and may be a function of, among other things, the intended application and/or desired functionality of the pre-object filter 700. For example, in one embodiment, where the pre-object filter 700 is substantially symmetrically shaped (e.g., where a first half of the filter extending from a midpoint of the core to the first end 704 is shaped similarly to a second half of the filter extending form the midpoint of the core to the second end 706)), the pre-object filter 700 may be configured to rotate substantially synchronously with the rotating gantry (e.g., the pre-object filter 700 and the rotating gantry may rotate at a same speed). When the rotating gantry is at 0 degrees (e.g., as shown in FIG. 3), the pre-object filter 700 may be configured such that the first rotational angle of the pre-object filter 700 may be facing the object (e.g., as illustrated in FIG. 8, causing a first amount (e.g., a minimum amount) of radiation to be attenuated by the pre-object filter 700 and thus causing the unattenuated fan-angle have a first value). As the rotating gantry rotates about the object, the pre-object filter 700 may be synchronously rotated about the filter axis. Thus, when the rotating gantry is at 90 degrees at illustrated in FIG. 4, the second rotational angle of the pre-object filter 700 may be facing the object (e.g., as illustrated in FIG. 9, causing a second amount (e.g., a maximum amount) of radiation to be attenuated by the pre-object filter 700 and thus causing the unattenuated fan-angle to have a second value (e.g., which is less than the first value)). If the pre-object filter 700 is substantially symmetric, as the rotating gantry continues to rotate away from 90 degrees, the pre-object filter 700 may continue to adjust an amount of radiation attenuation to correspond to a profile of the object (e.g., increasing an unattenuated fan-angle until 180 degrees and then decreasing the unattenuated fan-angle until 270 degrees). In this way, the profile of radiation attenuation may be substantially continuously re-shaped as the rotating gantry rotates about the object, for example.

In other modes, the pre-object filter 700 may not rotate synchronously with the rotating gantry and/or the pre-object filter 700 may be configured to oscillate between two or more rotational angles of the pre-object filter 700, for example.

Moreover, in yet another mode, the pre-object filter 700 may be configured to rotate to a specified rotational angle prior to and/or at a beginning of an examination of an object and may remain stationary during the remaining portion of the examination. For example, a pre-scan may be performed to determine a profile of the object and the pre-object filter 700 may be rotated about the filter axis to an angle that corresponds to the profile (e.g., and that causes radiation having a trajectory that contacts the object to be attenuated less than radiation having a trajectory that does not contact the object). In this way, in this mode, a profile of radiation attenuation may be re-shaped and/or an amount of radiation attenuation may be adjusted between examinations of various objects (e.g., or between examinations of a same object), but may not be re-shaped/adjusted during an examination of an object, for example.

Figure 10:
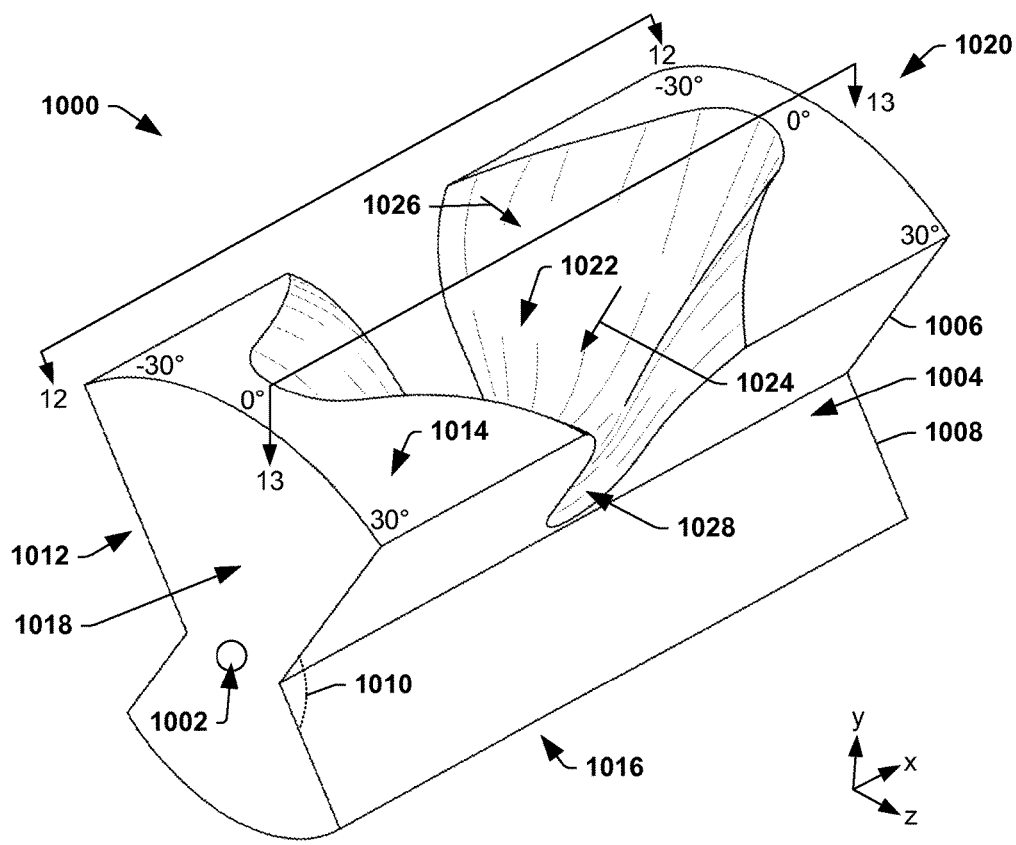
FIG. 10 illustrates an example pre-object filter.
Figure 11:
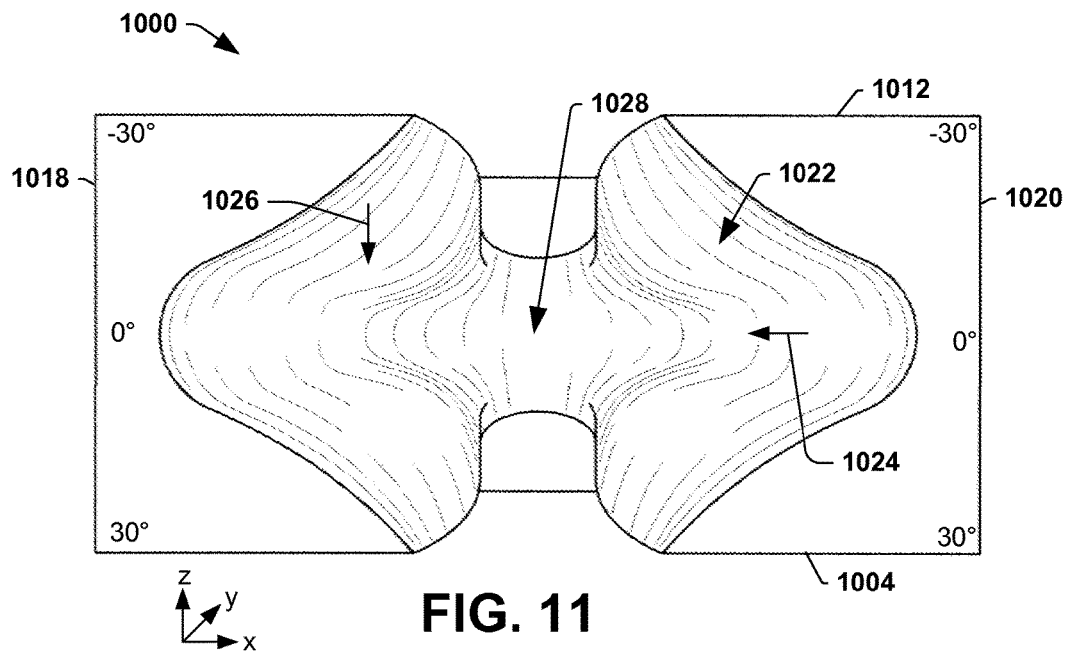
FIG. 11 illustrates an example pre-object filter.

FIGS. 10 and 11 illustrate views of yet another pre-object filter 1000 configured to shape a profile of radiation attenuation in a fan-angle direction as a function of a profile of an object being examined. In this way, an amount of radiation attenuated in the fan-angle direction (e.g., the x-direction) may be adjusted (e.g., altering an unattenuated fan-angle), before an imaging scan of an object is performed and/or during the imaging scan, based upon a shape, or profile, of the object, for example. Such a pre-object filter 1000 may be comprised of aluminum, cooper, Teflon, and/or other materials that are at least partially opaque to radiation, for example. In another embodiment, at least a portion of the pre-object filter 1000 may be comprised of a radiation transparent material(s).

The pre-object filter 1000 is configured for oscillation (e.g., partial rotation) about a filter axis extending in a direction (e.g., the x-direction) substantially perpendicular to the axis of rotation for a rotating gantry and/or substantially perpendicular to a trajectory of radiation emitted from a radiation source (e.g., which typically follows the y-direction). For example, in one embodiment, the pre-object filter 1000 may be configured to oscillate by about 60 degrees (e.g., between negative 30 degrees and positive 30 degrees as labeled on the pre-object filter 1000). Further, in one embodiment, the pre-object filter 1000 may be configured for translation in the fan-angle direction to track a region of interest and/or to track an object that is offset from a center line of the support article, for example.

The pre-object filter 1000 may comprise a bore 1002 through which a tube or a hollow core (e.g., 802 in FIG. 8) configured to rotate the pre-object filter 1000 may be inserted. In another embodiment, the pre-object filter 1000 may be machined with one or more flanges, for example, to replace the bore 1002, and a motor may be configured to connect to the flanges to oscillate the pre-object filter 1000, for example. Other manners and/or mechanisms for oscillating the pre-object filter 1000 are also contemplated.

A first surface 1004 of the pre-object filter 1000 is comprised of two inwardly sloping sidewalls 1006 and 1008

(e.g., sloping inward from an outside edge to a location proximate the bore 1002) that meet at a location proximate the bore 1002 at an angle 1010 other than 180 degrees (e.g., in one embodiment, 1010, it may be desirable for the angle 1010 to be small to reduce variability of the radiation in a cone-angle during the oscillation of the pre-object filter 1000). For example, in the illustrated embodiment, a first inwardly sloping sidewall 1006 and a second inwardly sloping sidewall 1008 join to form an angle 1010 of approximately 100 degrees. In another embodiment, the angle 1010 may be a different obtuse angle, a right angle, or an acute angle, for example. Moreover, in an embodiment, a second surface 1012, diametrically opposite the first surface 1004 relative to the bore 1002, is substantially symmetrical to the first surface 1004 (e.g., such that the second surface 1012 is approximately a mirror image of the first surface 1004), for example. A top surface 1014 and a bottom surface 1016 of the example pre-object filter 1000 are curved outward from the bore 1002 when viewed from a cross-section depicting a first end 1018 or a second end 1020 (e.g., where the second end 1020 is diametrically opposed to the first end 1018 relative to an aperture 1022 formed between the first end 1018 and the second end 1020).

The pre-object filter 1000 is shaped such that the aperture 1022 is formed between the first end 1018 and the second end 1020 and extends in a direction parallel to the filter axis (e.g., parallel to the x-direction). The aperture 1022 may slope 1024 inward from the first end 1018 and/or the second end 1020 to a center region (e.g., not shown) between the first end 1018 and the second end 1020. Thus, a depth of the aperture 1022 (e.g., measured in the y-direction from the top surface 1014) may be greater proximate the center region of the pre-object filter 1000 than at a location proximate the first end 1018 and/or the second end 1020. Moreover, the aperture 1022 may slope inward 1026 from the first surface 1004 and/or the second surface 1012 to a center region between the first surface 1004 and the second surface 1012. Thus, the aperture 1022 may slope inward toward a center region in both the x-direction and in the z-direction, for example. A channel 1028 may further extend across the pre-object filter 1000 in a direction substantially parallel to the axis of rotation (e.g., the z-direction) for a rotating gantry (e.g., the channel 1028 may extend in the z-direction) between the first surface 1004 and the second surface 1012 and may, in an example, have substantially uniform depth (e.g., measured in the y-direction from a top surface 1014) when moving from the first surface 1004 and the second surface 1012 or vice versa, for example. Although, the depth may change slightly due to changes in the curvature of the top surface 1014, for example.

FIG. 11 illustrates a top down view of the pre-object filter 1000 further illustrating how the aperture 1018 slopes inward toward a center region (e.g., proximate the channel 1028) from the first end 1018, the second end 1020, the first surface 1004, and/or the second surface 1012. FIG. 11 further illustrates the channel 1028 extending in a direction substantially parallel to the axis of rotation (e.g., the z-direction) and having a substantially uniform depth in the y-dimension, in an example.

In may be appreciated that as illustrated in FIGS. 10 and 11, the aperture 1022 has an increased width (e.g., measured in the x-direction) at 0 degrees, and decreases in width from 0 degrees toward the first surface 1004 and/or the second surface 1012 (e.g., at plus and/or minus 30 degrees). Such changes in width may provide for shaping (or reshaping) the profile of radiation attenuation as a function of a profile of an object during an imaging scan and/or between imaging scans, for example. That is, the portion of pre-object filter 1000 exposed to radiation or upon which radiation impinges may change by rotating or oscillating the pre-object filter, causing changes in a profile of radiation attenuation and/or causing an amount of radiation attenuated to vary.

Figure 12:
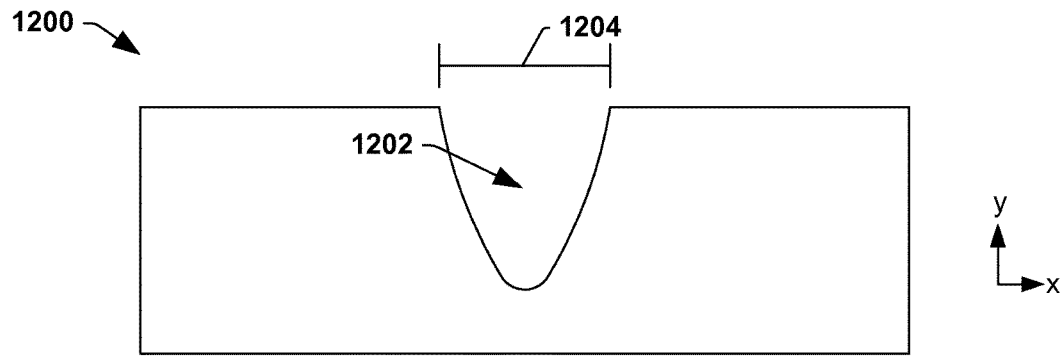
FIG. 12 illustrates a cross-section through an example pre-object filter.
Figure 13:
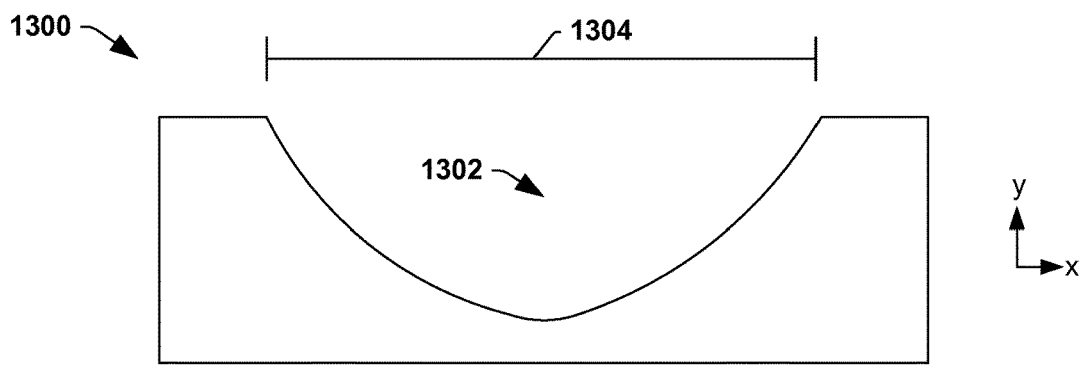
FIG. 13 illustrates a cross-section through an example pre-object filter.

By way of example, as illustrated in FIG. 12, a first cross-sectional slice 1200 (e.g., taking along line 12-12 in FIG. 10) may be exposed to radiation when the pre-object filter 1000 is rotated to negative 30 degrees (e.g., causing the radiation source to face the −30 degree mark in FIGS. 10 and 11). The first cross-sectional slice 1200 forms an aperture 1202 having a first width 1204 (e.g., which is approximately equal to the width of the channel 1028 illustrated in FIGS. 10 and 11). As illustrated in FIG. 13, a second cross-sectional slice 1300 (e.g., taking along line 13-13 in FIG. 10), different than the first cross-sectional slice, may be exposed to radiation when the pre-object filter 1000 is rotated to 0 degrees (e.g., causing the radiation source to face the 0 degree mark in FIGS. 10 and 11). The second cross-sectional slice 1300 forms an aperture 1302 having a second width 1304, which is different than (e.g., greater than) the first width 1202 of the aperture 1202. As such, an amount of radiation attenuated when the pre-object filter 1000 is rotated to negative 30 degrees may be different than an amount of radiation attenuated when the pre-object filter 1000 is rotated to 0 degrees. For example, given that the width of the aperture is greater at 0 degrees than at negative 30 degrees, more radiation may be attenuated at negative 30 degrees than at 0 degrees. Thus, the unattenuated fan-angle when the pre-object filter 1000 is rotated to negative 30 degrees may be less than the unattenuated fan-angle when the pre-object filter is rotated to zero degree. Moreover, as illustrated in FIG. 11, the width of the aperture 1022 may increase from negative 30 degrees to 0 degrees, and thus the unattenuated fan-angle may (e.g., gradually) increase and the amount of radiation attenuated may (e.g., gradually) decrease as the pre-object filter 1000 is rotated from negative 30 degrees to 0 degrees. It may be appreciated that a maximum depth of the aperture 1202 in FIG. 12 and a maximum depth of the aperture 1302 in FIG. 13 (e.g., measured in the y-direction) is typically substantially equal (e.g., and measure a depth of the channel 1028 in FIG. 11)

Although not shown, a cross-sectional slice exposed to radiation when the pre-object filter 1000 is rotated to 30 degrees may be substantially similar to the cross-sectional slice illustrated in FIG. 12. Thus, the amount of radiation attenuated may decrease at sequential rotational angles of the pre-object filter 1000 as the pre-object filter is rotated from negative 30 degrees to 0 degrees and may increase at sequential rotational angles of the pre-object filter 1000 as the pre-object filter is rotated from 0 degrees to 30 degrees, for example.

The pre-object filter 1000 is configured for partial rotation (e.g., or oscillation) about the filter axis, which is substantially perpendicular to an axis of rotation for a rotating gantry of a CT system. For example, the axis of rotation of the gantry may extend in the z-direction and the filter axis may extend in the x-direction. It may be appreciated that the degree of rotation may depend upon an angle 1010 formed by the joining of the first inwardly sloping sidewall 1008 and the second inwardly sloping sidewall 1006, as it may be desirable for radiation to traverse both a bottom portion of the pre-object filter (e.g., below the bore 1002 in FIG. 10) and a top portion (e.g., above the bore 1002 in FIG. 10). Movement of the pre-object filter 1000 may be controlled by a stepper motor or other motor, which may be controlled by a pre-object filter manipulator (e.g., 134 in FIG. 1), for example.

Numerous modes for at least partially rotating the pre-object filter 1000 about the filter axis are contemplated and may be a function of, among other things, the intended application and/or desired functionality of the pre-object filter 1000. For example, the pre-object filter 700 may be configured to oscillate between negative 30 degrees and 30 degrees during a rotation of the rotating gantry. By way of example, when the rotating gantry is at 0 degrees (e.g., as shown in FIG. 3), the pre-object filter 1000 may be configured such that a first rotational angle (e.g., 0 degrees) of the pre-object filter 1000 may be facing the radiation source (e.g., causing a first amount (e.g., a minimum amount) of radiation to be attenuated by the pre-object filter 1000 and thus causing the unattenuated fan-angle have a first value). As the rotating gantry rotates from 0 degrees to 90 degrees (e.g., as illustrated in FIG. 4), the pre-object filter 1000 may be rotated from the first rotational angle to a second rotational angle (e.g., 30 degrees) (e.g., causing a second amount (e.g., a maximum amount) of radiation to be attenuated by the pre-object filter 1000 and thus causing the unattenuated fan-angle to have a second value (e.g., which is less than the first value)). As the rotating gantry rotates from 90 degrees to 180 degrees, the pre-object filter 1000 may be rotated from the second rotational angle back to the first rotational angle (e.g., 0 degrees). Further, as the rotating gantry rotates from 180 degrees to 270 degrees, the pre-object filter 1000 may be rotated from the first rotational angle to a third rotational angle (e.g., negative 30 degrees). In this way, the pre-object filter 1000 is oscillated as a function of a gantry rotation angle, for example, and the profile of radiation attenuation is substantially continuously re-shaped as the rotating gantry rotates about the object, for example.

Moreover, in yet another mode, the pre-object filter 1000 may be configured to rotate to a specified rotational angle prior to and/or at a beginning of an examination of an object and may remain stationary during the remaining portion of the examination. For example, a pre-scan may be performed to determine a profile of the object and the pre-object filter 1000 may be rotated about the filter axis to an angle that corresponds to the profile (e.g., or to a largest dimension of the object being scanned). In this way, in this mode, a profile of radiation attenuation may be re-shaped and/or an amount of radiation attenuation may be adjusted between examinations of various objects (e.g., or between examinations of a same object), but may not be re-shaped/adjusted during an examination of an object, for example.

It may be appreciated that the foregoing pre-object filters are merely provided as example configurations of pre-object filters that may be utilized to shape a profile of radiation attenuation as a function of a profile of an object and are not intended to limit the scope of the instant disclosure, including the scope of the claims. Moreover, it may be appreciated that the illustrated pre-object filters may comprise readily apparent features which are not described.

Figure 14:
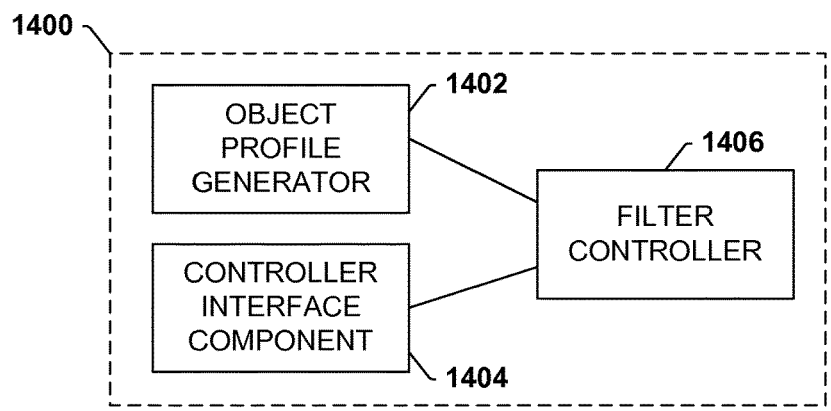
FIG. 14 illustrates an example pre-object filter manipulator.

FIG. 14 illustrates an example pre-object filter manipulator 1400 (e.g., 134 in FIG. 1) configured to control motion (e.g., translation and/or rotation) of a pre-object filter (e.g., such as one or more of the foregoing pre-object filters) as a function of, among other things, a profile of an object undergoing an examination, a gantry rotation angle of the rotating gantry, and/or a translation coordinate and speed of the object (e.g., as indicated by movement of a support article supporting the object).

The example pre-object filter manipulator 1400 comprises, among other things, an object profile generator 1402, a controller interface component 1404, and a filter controller 1406. The object profile generator 1402 is configured to create a profile of the object based upon information provided by a source such as, for example, a user (e.g., which may provide one or more measurements of the object) and/or a pre-scan (e.g., also referred to as a scout scan) of the object. Such a pre-scan may comprise performing an initial (e.g., low-dose) examination using a CT system and/or performing an examination using a line scanner at an entrance of the CT scanner, for example. Pre-scan information generated from such a pre-scan may be provided to the object profile generator 1402 via a terminal and/or a controller, for example. Typically, the pre-scan information is insufficient to reconstruct an image of the object. However, using such information, the object profile generator may determine a relative orientation of a support article and the object, one or more measurements (e.g., dimensions) of the object, etc. from which to create the profile of the object. Thus, using pre-scan information and/or user input, for example, the object profile generator 1402 may create a profile of the object.

The controller interface component 1404 may be configured to interface with a controller (e.g., 132 in FIG. 1) and to receive information related to an examination unit (e.g., 108 in FIG. 1) which may assist in determining when and/or how to rotate and/or translate the pre-object filter. For example, the controller interface component 1404 may receive information indicative of a rotation speed of a rotating gantry (e.g., 104 in FIG. 4) and/or a gantry rotational angle of the rotating gantry. As another example, the controller interface component 1404 may receive information indicative of a translation coordinate of a support article configured to support the object (e.g., to determine which aspect/cross-section of the object is presently being exposed to radiation).

The profile of the object created by the object profile generator 1402 and/or information from the controller interface component 1404 may be received by the filter controller 1406 configured to manipulate the pre-object filter to shape the profile of radiation attenuation in the fan-angle direction. For example, as previously described, a shape of a profile may be changed based upon a profile of the object, a gantry rotational angle, and/or a position of the support article, for example. Thus, the filter controller 1406 may be configured to manipulate (e.g., or generate manipulation instructions) for controlling how the pre-object filter is to be moved to shape a profile of radiation attenuation, for example.

Figure 15:
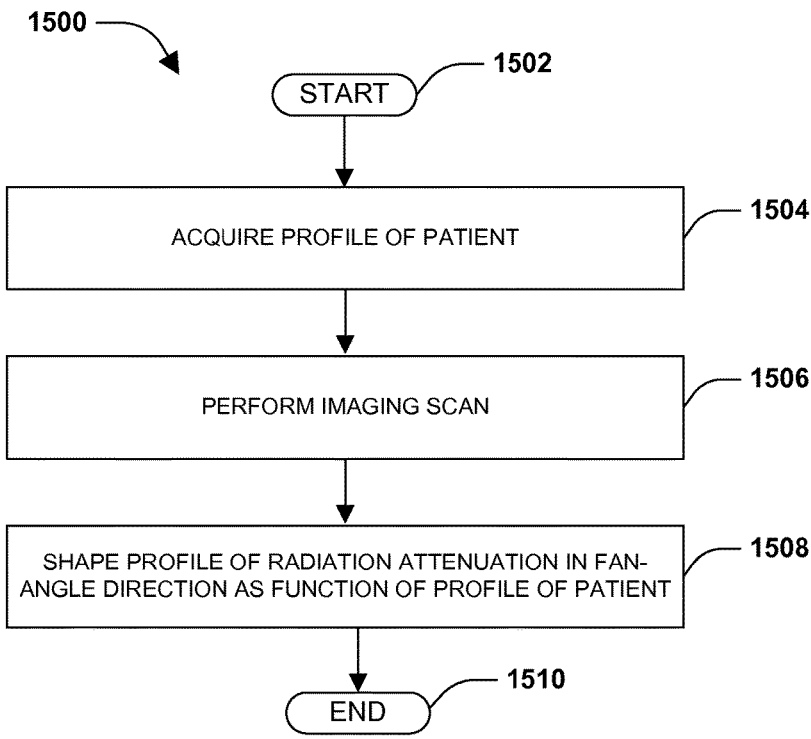
FIG. 15 illustrates an example method for imaging a patient.

FIG. 15 illustrates an example method 1500 for imaging a patient and/or object, such as via a computed tomography (CT) system or other imaging system. The example method 1500 begins at 1502, and a profile of the patient is acquired at 1504. The profile describes one or more features of the patient, such as a shape, size (e.g., measurements), and/or orientation relative to a support article supporting the patient. Such a profile may be acquired manually and/or automatically. For example, measurements corresponding to a size of the patient may be input by a user and/or a pre-scan may be performed to determine shape, size, and/or orientation information from which an object profile may be developed.

At 1506 in the example method, an imaging scan is performed on the patient. The imaging scan typically involves exposing the patient to a sufficient dose from which an image of a desired quality may be produced. During the imaging scan, the patient is exposed to radiation, some of which traverse the patient. Information yielded from the radiation that traversed the patient may be utilized to generate/reconstruct an image(s). Such an image may be a two-dimensional image, a three-dimensional image, a four dimensional image, etc. Moreover, the imaging scan may involve viewing the patient from a single angle (e.g., such as in projection scanning), viewing the patient from a multitude of angle (e.g., such as in tomosynthesis scanning), and/or viewing the patient from at least 180 degrees (e.g., such as in CT scanning).

At 1508 in the example method 1500, a profile of radiation attenuation in a fan-angle direction is shaped as a function of the profile of the patient to affect an amount of radiation attenuated in a fan-angle direction. As previously described, the shaping may occur at least one of prior to performing the imaging scan and/or during the imaging scan is a function of the profile of the patient. Thus, a profile of radiation attenuation for a first patient may be different than a profile of the radiation attenuation for a second patient and/or the profile of attenuation may change during a rotation (e.g., to change as (e.g., cross-sectional) size of the patient as viewed from various angles changes).

To shape the profile of the radiation attenuation, one or more of the foregoing techniques (e.g., modes) and/or pre-object filters may be utilized. For example, in one embodiment, shaping the profile of radiation attenuation may comprise translating the pre-object filter in a direction parallel to an axis of rotation for a rotating gantry of an imaging system configured to perform the imaging scan and/or parallel to the z-direction (e.g., as described with respect to FIGS. 5-6). In another embodiment, shaping the profile of radiation attenuation may comprise rotating and/or oscillating the pre-object filter about a filter axis that is parallel to the x-direction, for example (e.g., such as described with respect to FIGS. 7-13). By way of example, in one embodiment, the pre-object filter may be oscillated between a first position and a second position (e.g., separated by less than a specified amount, such as by less than 60 degrees, for example). In another embodiment, the pre-object filter may be configured for complete rotation about the filter axis and may, in one embodiment, be synchronized with the rotation of the rotating gantry, for example.

The example method 1500 ends at 1510.

Figure 16:
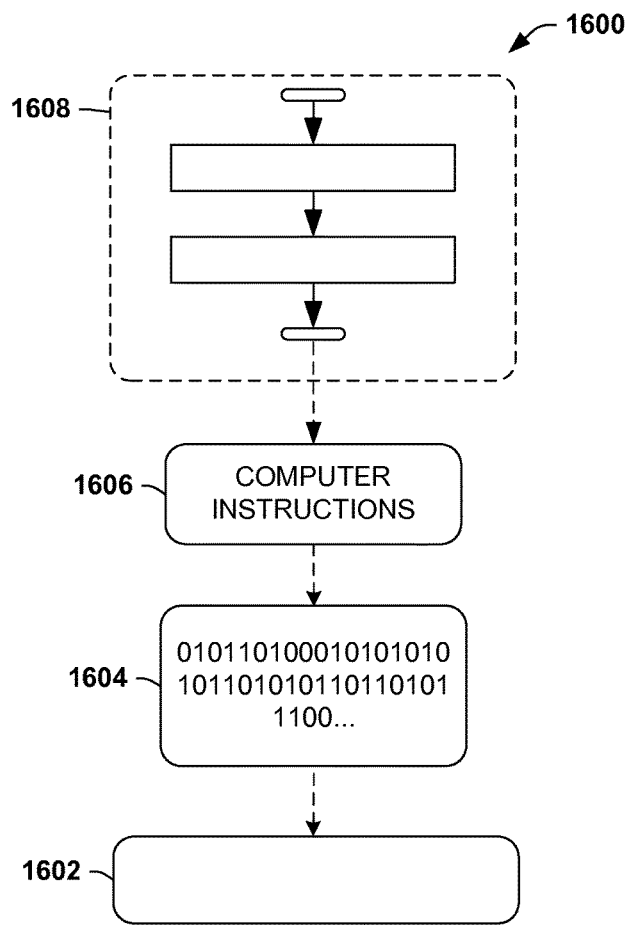
FIG. 16 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 16, wherein the implementation 1600 comprises a computer-readable medium 1602 (e.g., a CD-R, DVD-R, or a platter of a hard disk drive), on which is encoded as processor-executable instructions 1604. This computer-readable data 1604 in turn comprises a set of computer instructions 1606 configured to operate according to one or more of the principles set forth herein. In one such embodiment 1600, the processor-executable instructions 1604 may be configured to perform a method 1608, such as at least some of the example method 1500 of FIG. 15. In another such embodiment, the processor-executable instructions 1604 may be configured to implement a system, such as at least some of the exemplary environment 100 of FIG. 1 and/or at least some of example pre-object filter manipulator 1400, for example. Many such computer-readable media may be devised by those of ordinary skill in the art that are configured to operate in accordance with one or more of the techniques presented herein.

Moreover, "exemplary" is used herein to mean serving as an example, instance, illustration, etc., and not necessarily as advantageous. As used in this disclosure, "or" is intended to mean an inclusive "or" rather than an exclusive "or." In addition, "a" and "an" as used in this disclosure are generally be construed to mean "one or more" unless specified otherwise or clear from context to be directed to a singular form. Also, at least one of A and B and/or the like generally means A or B or both A and B. Furthermore, to the extent that "includes," "having," "has," "with," or variants thereof are used in either the detailed description or the claims, such terms are intended to be inclusive in a manner similar to the term "comprising."

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used in this disclosure, "component," "module," "system," "interface," and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Further, unless specified otherwise, "first," "second," and/or the like are not intended to imply a temporal aspect, a spatial aspect, an ordering, etc. Rather, such terms are merely used as identifiers, names, etc. for features, elements, items, etc. (e.g., "a first channel and a second channel" generally corresponds to "channel A and channel B" or two different (or identical) channels).

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application.

What is claimed is:

1. An apparatus for a computed tomography (CT) system, comprising:
a pre-object filter configured to shape a profile of radiation attenuation in a fan-angle direction as a function of a profile of an object being examined, wherein:
the pre-object filter is configured to rotate about an axis,
the pre-object filter has a first surface defined by a first sidewall abutting a top surface of the pre-object filter and sloping toward the axis and a second sidewall abutting a bottom surface of the pre-object filter and sloping toward the axis,
the first sidewall extending from a first end of the pre-object filter to a second end of the pre-object filter,
the second sidewall extending from the first end to the second end,
the pre-object filter has a channel extending across the pre-object filter from the first surface to a second surface diametrically opposite the first surface,
the channel is disposed between the first end and the second end,
an aperture is defined by an inner wall of pre-object filter abutting the first sidewall and the top surface, and
the inner wall slopes from the top surface of the pre-object filter toward the channel.

2. The apparatus of claim 1, comprising:
an object profile generator configured to determine at least one measurement of the object from which to create the profile.

3. The apparatus of claim 1, wherein the channel extends perpendicular to the axis.

4. The apparatus of claim 1, wherein a longest dimension of the first surface extends parallel to the axis.

5. The apparatus of claim 3, wherein the aperture has a first width at a first location extending in a direction parallel to the channel and a second width at a second location extending in the direction parallel to the channel.

6. The apparatus of claim 1, wherein a distance between the axis and a bottom of the channel is uniform.

7. The apparatus of claim 1, wherein the pre-object filter is configured to attenuate a first amount of radiation at a first rotational angle of the pre-object filter and to attenuate a second amount of radiation at a second rotational angle of the pre-object filter.

8. The apparatus of claim 1, wherein the pre-object filter is configured for translation in a direction parallel to the axis.

9. The apparatus of claim 8, wherein pre-object filter is translated in the direction parallel to the axis of when the profile of the object indicates that the object is offset relative to a center line of a support article supporting the object, the center line substantially parallel to an axis of rotation for a rotating gantry of the CT system.

10. A method for imaging a patient, comprising:
acquiring a profile of the patient, the profile describing one or more features of the patient;
performing an imaging scan on the patient; and
shaping, as a function of the profile of the patient, a profile of radiation attenuation in a fan-angle direction to affect an amount of radiation attenuated in the fan-angle direction, wherein the shaping comprises:
translating, in the fan-angle direction, a pre-object filter configured to shape the profile of radiation attenuation when a center line of the patient is offset from a center line of a support article supporting the patient, the center line of the support article substantially parallel to an axis of rotation about which a rotating gantry supporting a radiation source rotates during the imaging scan.

11. The method of claim 10, the shaping comprising:
translating the pre-object filter in a direction substantially parallel to the axis of rotation.

12. The method of claim 10, comprising:
oscillating a pre-object filter configured to shape the profile of radiation attenuation about a filter axis substantially parallel to the fan-angle direction, wherein the pre-object filter is oscillated between a first position and a second position, the first position separated from the second position by less than about 60 degrees.

13. A computed tomography (CT) system, comprising:
a radiation source;
a detector array;
a rotating gantry configured to rotate the radiation source and the detector array about an object under examination; and
a pre-object filter positioned between the radiation source and the object and configured to shape a profile of radiation attenuation as a function of a profile of the object, wherein:
the pre-object filter comprises a planar first sidewall extending from a first end of the pre-object filter to a second end of the pre-object filter,
a channel is defined that extends from the planar first sidewall toward a second sidewall diametrically opposite the planar first sidewall, wherein the channel is disposed between the first end and the second end, and
the channel extends in a direction parallel to an axis about which the rotating gantry rotates.

14. The CT system of claim 13, wherein a longest dimension of the planar first sidewall extends in the direction parallel to the axis about which the rotating gantry rotates.

15. The CT system of claim 13, wherein the pre-object filter is configured to be translated in the direction parallel to the axis about which the rotating gantry rotates.

16. The CT system of claim 15, comprising:
a filter controller configured to translate the pre-object filter in the direction parallel to the axis about which the rotating gantry rotates to shape the profile of radiation attenuation.

17. The CT system of claim 1, wherein:
a bore is defined by the first end at the axis.

18. The CT system of claim 17, wherein:
the bore extends from the first end to the second end.

19. The CT system of claim 13, comprising:
an object profile generator configured to determine at least one measurement of the object from which to create the profile of the object.

20. The CT system of claim 13, wherein a third sidewall of the pre-object filter that defines the channel abuts a top surface of the pre-object filter to define a rounded corner.

* * * * *